United States Patent [19]
Sano et al.

[11] Patent Number: 5,118,179
[45] Date of Patent: Jun. 2, 1992

[54] OPTHALMOLOGICAL PHOTOGRAPHING INSTRUMENT

[75] Inventors: Eiichi Sano; Hideaki Tokoro, both of Tokyo, Japan

[73] Assignee: Kabushiki Kaisha Topcon, Japan

[21] Appl. No.: 514,020

[22] Filed: Apr. 26, 1990

[30] Foreign Application Priority Data

Apr. 26, 1989 [JP] Japan .................................. 1-106350

[51] Int. Cl.⁵ .............................................. A61B 3/14
[52] U.S. Cl. .................................... 351/206; 351/207
[58] Field of Search ....................... 351/206, 221, 207; 354/62

[56] References Cited

U.S. PATENT DOCUMENTS 4,436,388  3/1984  Takahashi et al. .................. 351/206

Primary Examiner—Paul M. Dzierzynski
Attorney, Agent, or Firm—Finnegan, Henderson, Farabow, Garrett & Dunner

[57] ABSTRACT

An ophthalmological photographing instrument has photographing means for imaging the fundus of an eye to be tested every time a photographing switch is actuated, and a barrier filter to be inserted into a photographing optical path when a fluorescence photography is performed. It also has a light receiving sensor for receiving fluorescence emitted from the eye fundus and control means for inserting the barrier filter into the taking optical path every time the taking switch is actuated when a light receiving signal output from the eye fundus becomes either larger or smaller than a predetermined value.

10 Claims, 5 Drawing Sheets

OPTHALMOLOGICAL PHOTOGRAPHING INSTRUMENT

BACKGROUND OF THE INVENTION

1. Field of the Invention

This invention relates to an ophthalmological taking instrument in which a barrier filter is inserted into a photographing optical path at the time when a fluorescence photography is taken.

2. Prior Art of the Invention

Heretofore, when an eye fundus is taken by fluorescence photography, a fluorescent agent is injected to the vein of the patient. The fluorescence photography is performed in such a manner as that when a fluorescent agent circulates within the body of the patient and the fluorescent agent appears on the eye fundus, the eye fundus is illuminated with an exciting light of a predetermined wavelength so that fluorescence of a predetermined wavelength is emitted from the fluorescent agent on the eye fundus. At the time when the eye fundus is taken by fluorescence photography, an exciter filter for permitting an exciting light of a predetermined wavelength to transmit therethrough is inserted into an illuminating optical path and a barrier filter for permitting fluorescence of a certain wavelength to transmit therethrough and removing the exciting light of a predetermined wavelength is inserted into the photographing optical path.

The quantity of the fluorescent agent flowing in the blood vessel of the eye fundus, as shown in FIG. 6, is gradually increased in initial period T after the passage of a predetermined time from the time when the fluorescent agent is injected. The agent is abruptly increased in quantity in a middle period T2 and begins to appear on the entire eye fundus. In a latter time period T3, the quantity of the fluorescent agent is considerably reduced and further gradually reduced with the passage of time.

As a consequence, in the latter time period T3, because brightness of the fluorescence is low and the barrier filter is inserted in the photographing optical path, the whole eye fundus is observed dim. Therefore, as the alignment becomes difficult to perform, it is necessary for the examiner to increase the quantity of the illumination light.

However, when taking into consideration possible damage to the retina of the eye, it is undesirable to increase the quantity of the illumination light more than necessary. Therefore, there is such a problem as that alignment is difficult to perform in the later time period T3.

SUMMARY OF THE INVENTION

An object of the present invention is to provide an ophthalmological photographing instrument in which alignment can be easily performed even in a latter time period of circulation of a fluorescent agent.

Another object of the present invention is to provide an ophthalmological photographing instrument in which a barrier filter is automatically inserted in accordance with a circulation time of a fluorescent agent.

A feature of the present invention is that an ophthalmological photographing instrument comprises a light receiving sensor for receiving fluorescence emitted from the fundus of an eye to be tested, and control means for inserting a barrier filter into a photographing optical path every time a taking switch is operated when a light receiving signal output from the eye fundus becomes smaller than a predetermined value.

Another feature of the present invention is that an ophthalmological photographing instrument comprises a judgment means for judging an initial time period where fluorescence appears on the fundus of eye to be tested, a middle time period where the fluorescence begins to spread over the entire eye fundus and a latter time period where the fluorescence becomes gradually weak, and control means for controlling insertion and removal of the barrier filter into and from a photographing optical path based on the time periods which the judgment means judges.

DETAILED DESCRIPTION OF THE EMBODIMENT

The embodiment of an ophthalmological photographing instrument according to the present invention will be described hereunder with reference to the accompanying drawings.

Figure 1:
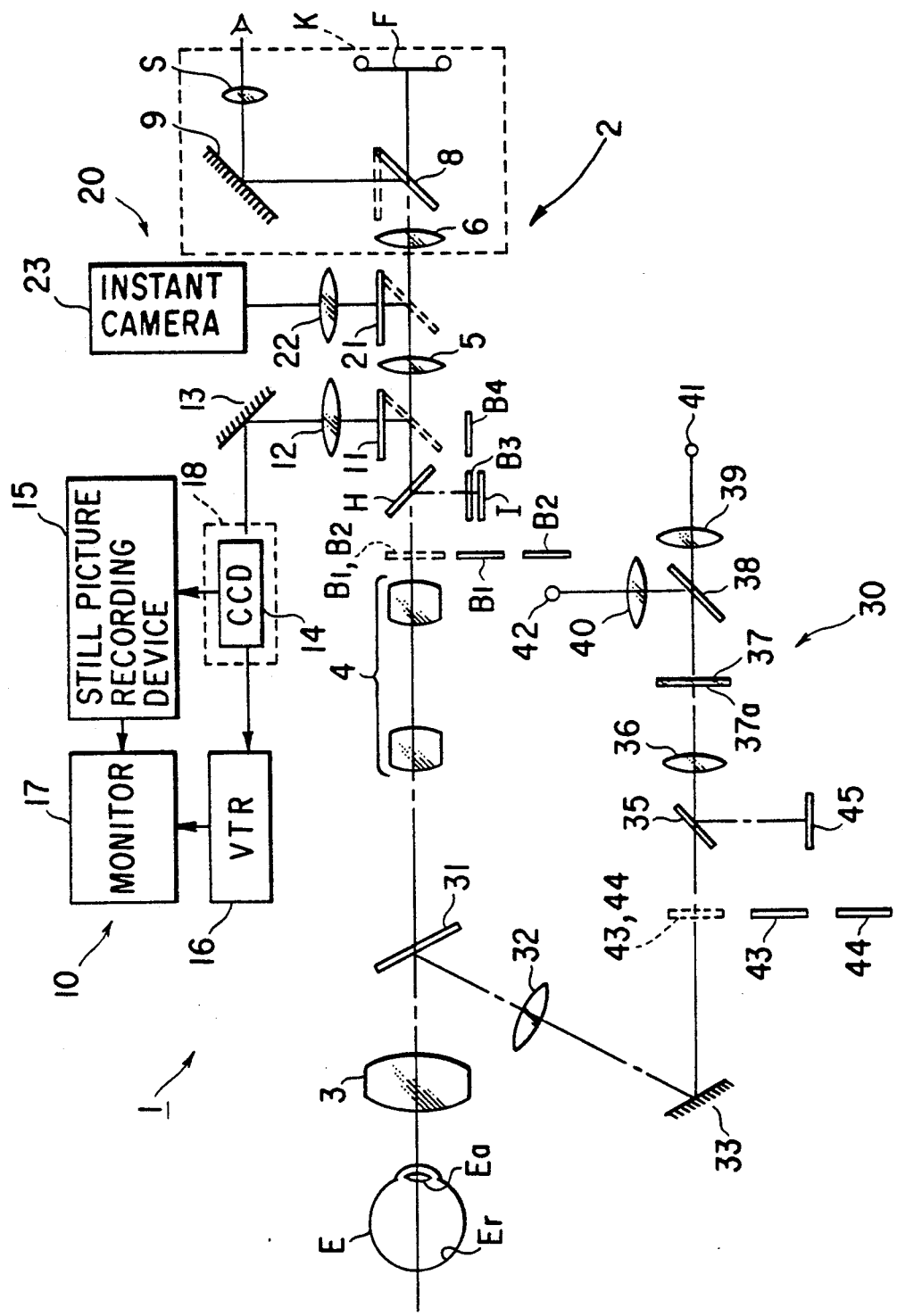
FIG. 1 is a diagrammatic view showing the arrangement of an optical system of an ophthalmological photographing instrument according to the present invention.

An optical system of an ophthalmological photographing instrument shown in FIG. 1 includes an observation system 1 for observing the fundus Er of an eye E to be tested, and an illumination optical system 30 for illuminating the fundus Er of the eye E to be tested.

The observation system 1 comprises an observation optical system 2 including a 35 mm camera (photographing), an electronic camera photographing optical system which shares a portion of an optical axis of the observation optical system 2, and an instant camera photographing optical system 20 which shares a portion of an optical axis of the observation optical system 2.

The observation optical system 2 comprises an objective lens 3 placed opposite the eye E to be tested, a focusing lens 4, a relay lens 5, a photographing lens 8, mirrors 8,9, and eyepiece S. Also, the observation optical system 2 is provided with a light receiving sensor (area sensor) I for receiving fluorescence emitted from the eye fundus Er through a half mirror H, a visible fluorescence barrier filter B1 and an infrared fluorescence barrier filter B2. The area sensor I comprises a CCD, for example.

The visible fluorescence barrier filter B1 and the infrared fluorescence barrier filter B2 are movable to a position outside the optical path shown by a solid line and a position within the optical path shown by a broken line. Furthermore, in front of the area sensor I, a visible fluorescence barrier filter B3 and an infrared fluorescence barrier filter B4 are arranged, so that the barrier filter B3 is inserted into the optical path when in a visible fluorescence mode and the barrier filter B4 is inserted into the optical path when in an infrared fluorescence mode. By virtue of the provisions of these barrier filters B3 and B4, the area sensor I functions as detection means for detecting fluorescence emitted from the eye fundus Er.

The mirror 8 is designed such that it jumps up to the position shown by the broken line when photographing. The reference character F denotes a 35 mm film.

The electronic camera taking optical system 10 includes a mirror 11 which moves to the position shown by the broken line when photographing, a relay lens 12, a mirror 13, and a television camera TV (moving picture taking means) 18 having a CCD 14 for receiving an image of the eye fundus. The numeral 15 denotes a still picture recording device (a still picture photographing means) such as an electronic still camera or the like which is connected to the CCD 14, and the numeral 16 denotes a VTR connected to the CCD 14. The numeral 17 denotes a monitor for displaying an image of the eye fundus which is taken by a still picture recording device and an image of the eye fundus which is recorded in the VTR 16.

The mirror 11 is moved to the position shown by the broken line when in an infrared fluorescence mode, so that they eye fundus Er can be observed through the monitor 17.

The instant camera optical system 20 includes a mirror 21 which is moved to the position shown by the broken line when photographing, a relay lens 22, and an instant camera (photographing means) 23.

The illumination optical system 30 includes an objective lens 3, a perforated mirror 31, a relay lens 32, a mirror 33, a half mirror 35, a relay lens 36, a ring aperture plate 37 placed in a position conjugate with the pupil Ea, a half mirror 38, relay lenses 39,40, an illumination light source 41, and a taking light source 42. The ring aperture plate 37 is provided with a ring-shaped aperture 37a formed thereon.

The illumination optical system 30 is provided with a visible fluorescence exciter filter 43 and an infrared fluorescence exciter filter 44, and a light receiving sensor 45 for controlling the light quantity of the illumination light source 41 and the taking light source 42. The visible fluorescence exciter filter 43 and the infrared fluorescence exciter filter 44 are designed such that they can be moved to the position outside the optical path shown by the solid line and the position within the optical path shown by the broken line.

When an illumination light is emitted from the illumination light source 41, the illumination light is made incident to the eye E through the relay lens 39, the half mirror 38, the ring aperture plate 37, the relay lens 36, the half mirror 35, the mirror 33, the relay lens 32, the perforated mirror 31 and the objective lens 3. An aperture image of the ring aperture 37a is formed on the pupil Ea, and the eye fundus Er is illuminated by this aperture image.

A reflected beam from the eye fundus Er reaches the eyepiece S through the objective lens 3, the perforated mirror 31, the focusing lens 4, the half mirror H, the relay lens 5, the photographing lens 6 and the mirrors 8,9, and the eye fundus Er can be observed.

When the eye fundus Er is being photographed, if the mirror 8 is jumped up to the position shown by the broken line and the photographing light source 42 is flashed, the eye fundus Er can be photographed by the 35 mm camera K, and if the mirrors 11, 21 are shifted to the respective positions shown by the broken lines, the eye fundus Er can be respectively photographed by the TV camera 18 and the instant camera 23. When the eye fundus Er is photographed by the instant camera 23, the photographing light source 42 is flashed in the same manner as mentioned above. When the eye fundus Er is photographed by the still picture recording device 15, the photographing light source 42 may also be flashed.

Figure 2:
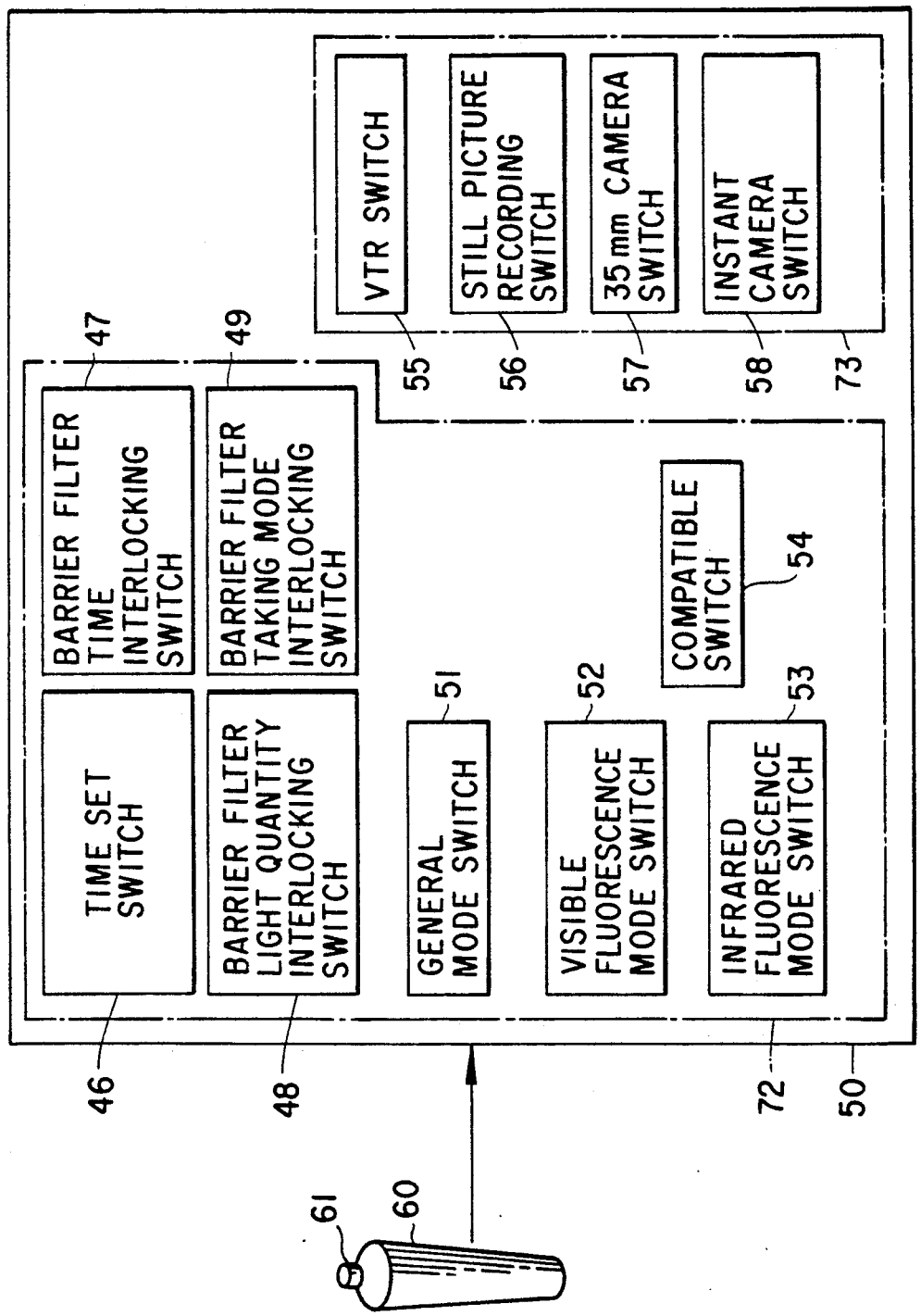
FIG. 2 is an explanatory view showing a positional relation of respective switches arranged on a control box.

FIG. 2 shows the arrangement of respective switches provided on a control box 50 of the ophthalmological photographing instrument. The numeral 51 denotes a general mode switch which is pressed when a normal photography other than a fluorescence photography is performed. If this switch 51 is pressed when the barrier filters B1, B2 and the exciter filter 43, 44 are inserted in the optical path, the filters B1, B2, 43 and 44 in positions within the optical path shown by the broken line in FIG. 1 are moved to the positions outside the optical path shown by the solid line. The numeral 52 denotes a visible fluorescence mode switch which is pressed when a visible fluorescence photography is performed. When this switch 52 is pressed, the visible fluorescence exciter filter 43 is inserted into the position within the optical path shown by the broken line from the position outside the optical path shown by the solid line of FIG. 1. In this case, the barrier filter B3 is already inserted in the optical path.

The numeral 53 denotes an infrared fluorescence mode switch which is pressed when an infrared fluorescence photography is performed. When this switch 53 is pressed, the infrared fluorescence exciter filter 44 is moved from the position shown by the solid line to the position shown by the broken line. In this case, the barrier filter B4 instead of the barrier filter B3 id already inserted in the optical path.

The numeral 54 denotes a compatible switch which is pressed when photography is performed by the VTR 16 in the middle time period T2 (see FIG. 6), and by the still picture recording device 15, the 35 m film F, the instant camera 23, et. in the latter time period T3. The numeral 55 denotes a VTR selection switch (selection means) which is pressed when photography is performed by the TV camera 18 and the picture is recorded by the VTR 16. The numeral 56 denotes a still picture recording device selection switch (selection means) which is pressed when photography is performed by the still image recording device. The numeral 57 denotes a 35 mm selection switch (selection means) which is pressed when photography is performed by the 35 mm camera K, and the numeral 58 denotes an instant camera selection switch (selection means) which is pressed when photography is performed by the instant camera.

The numeral 46 denotes a time set switch for setting time in the middle stage time period in the circulation time.

The time set switch 46 sets the time in the middle stage time period by preliminarily judging the initial time period, the middle time period and the latter time period of the circulation time of the fluorescent agent from the passage of time after the fluorescent agent is injected. The numeral 47 denotes a barrier filter time interlocking switch for inserting the barrier filters B1, B2 into the photographing optical path at the time set by the time set switch 46.

The numeral 48 denotes a barrier filter light quantity interlocking switch. The barrier filter light quantity interlocking switch 48 is adapted to move the barrier filters B1, B2 to the positions within the taking optical path shown by the broken line in the initial time period or middle time period when a controller 70, as will be described later, judges the initial time period, middle time period, and latter time period on the basis of the light receiving quantity of the area sensor I. The numeral 49 denotes a barrier filter photographing mode interlocking switch for inserting the barrier filters B1 and B2 into the photographing optical path when the eye fundus Er is being photographed by the TV camera 18.

The numeral 60 denotes a joy stick for performing alignment, etc. by moving the body of the ophthalmological photographing instrument (not shown), and the numeral 61 denotes a joy stick switch (taking switch) which is pressed when photography is performed. When this joy stick switch 61 is pressed, an ON-signal is input into the controller 70 (see FIG. 3) within the control box 50.

Figure 3:
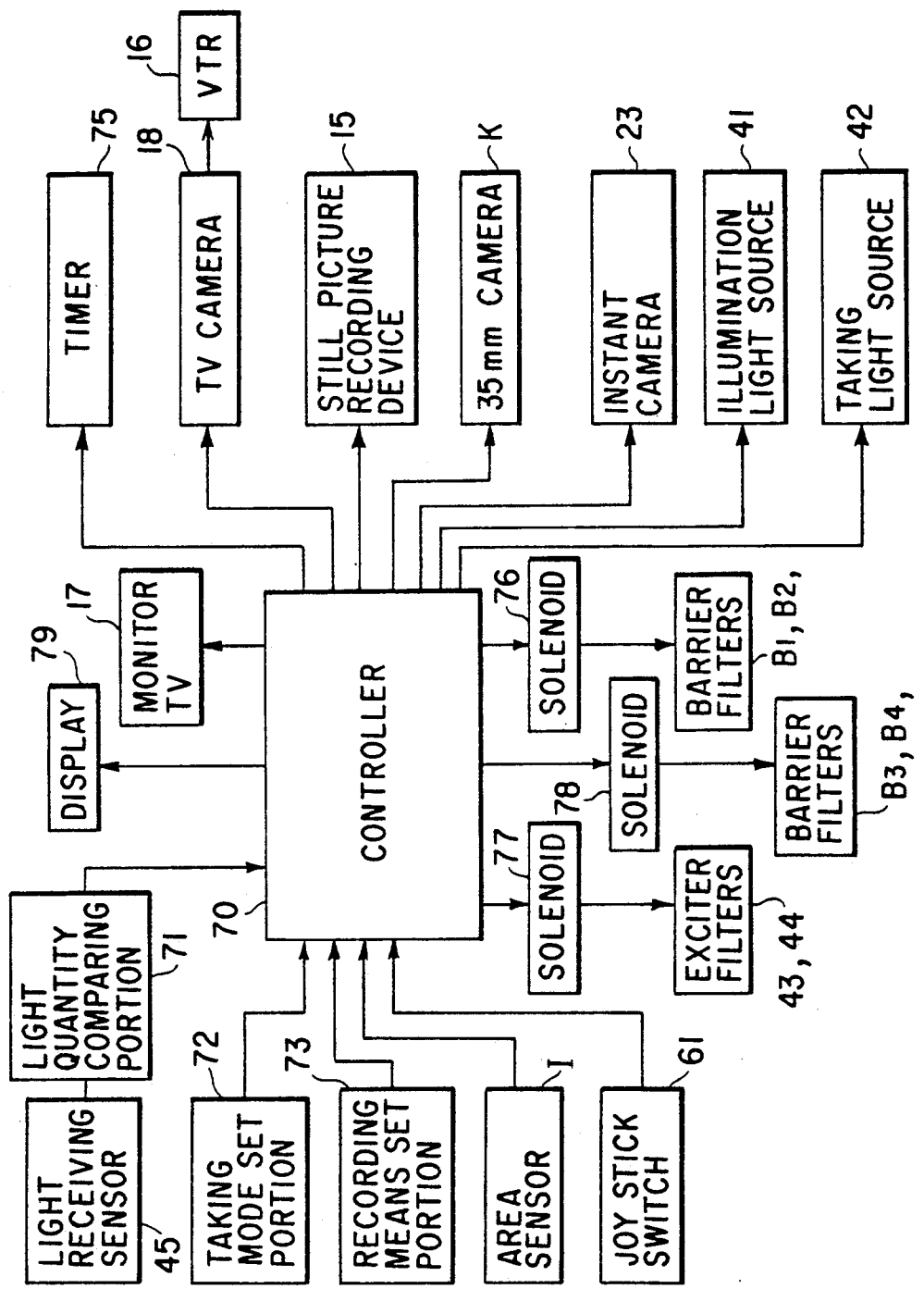
FIG. 3 is a block diagram showing the construction of a control system of the ophthalmological photographing instrument.

FIG. 3 is a block diagram showing the construction of a control system of the ophthalmological photographing instrument. In FIG. 3, the numeral 71 denotes a light quantity comparing portion for comparing the value of a light receiving signal output from the light receiving sensor 45 with a reference set value preliminarily set, and outputting a comparing signal when the value becomes larger than the reference set value. The light comparing portion 71 is adapted to control the light emitting quantities of the illuminate light source 41 and photographing light source 42. The numeral 72 denotes a photographing mode set portion including the time set switch 46, the respective interlocking switches 47 through 49, the respective mode switched 51 through 53, the compatible switch 54, etc. shown in FIG. 2, and the numeral 73 denotes recording means set portion comprising various selection switches 55 through 58. The numeral 75 denotes a timer for counting the passage of time after the vein injection is effected. Display time showing the time counted by this timer is recorded in the VTR 16 when photography is performed by the TV camera 18.

The numeral 76 denotes a solenoid adapted to move the visible fluorescence filter B1 and the infrared fluorescence filter B2 from the positions shown by the solid line of FIG. 1 to the positions shown by the broken line, or from the positions shown by the broken line to the positions shown by the solid line in accordance with a command from the controller 70. The numeral 77 denotes a solenoid adapted to move the visible fluorescence exciter filter 43 and the infrared fluorescence exciter filter 44 from the positions shown by the solid line of FIG. 1 to the positions shown by the broken line, or from the positions shown by the broken line to the positions shown by the solid line. The numeral 78 denotes a solenoid adapted to insert the barrier filter B3 into the optical path when in the visible fluorescence mode and insert the barrier filter B4 into the optical path when in the infrared fluorescence mode. The numeral 79 denotes a display (display means) for displaying detection when fluorescence is detected by the area sensor I.

Figure 6:
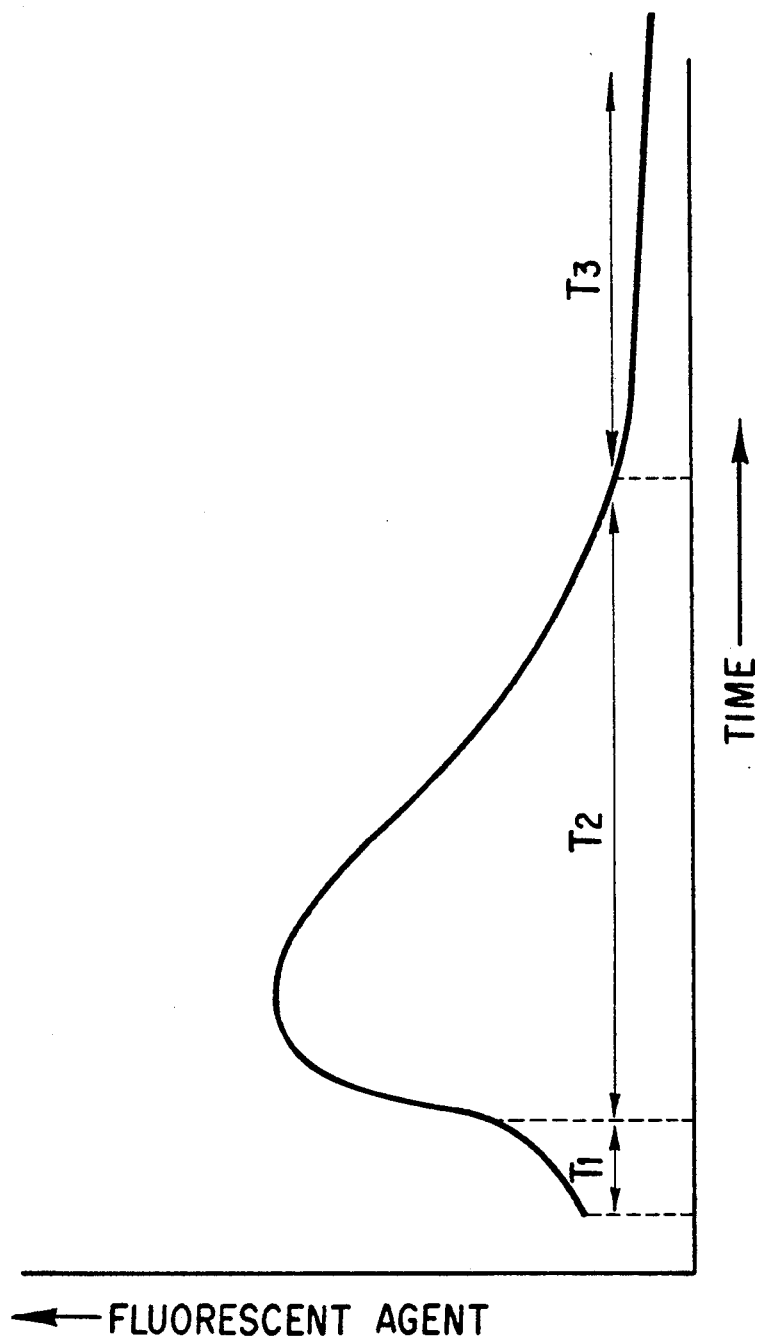
FIG. 6 is a graph schematically showing a relation between a fluorescent agent flowing into the eye fundus and the passage of time.

The controller 70 has a function acting as judgment means for judging the initial time period T1, the middle time period T2 and the latter time period T3 of FIG. 6 based on the light receiving signal output from the area sensor I, and a function acting as control means for controlling the solenoid 76 and inserting or removing the barrier filters B1, B2 into or from the taking optical path based on the judgment.

Also, upon depression of the barrier filter time interlocking switch 47, the controller 70 inserts the barrier filters B1, B2 into the photographing optical path when the time counted by the timer 75 becomes the time (middle time period T2) set by the time set switch 46. In this case, the controller 70 judges the initial time period T1, the middle time period T2 and the latter time period T3 from the time counted by the timer.

Figure 4:
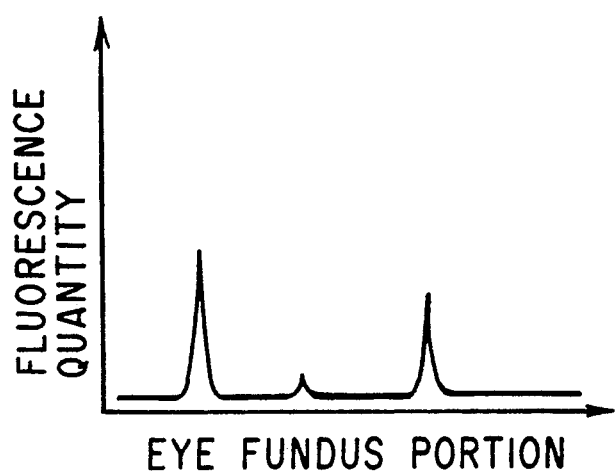
FIG. 4 is a graph showing the quantity of fluorescence of the eye fundus which appears in the initial time period.
Figure 5:
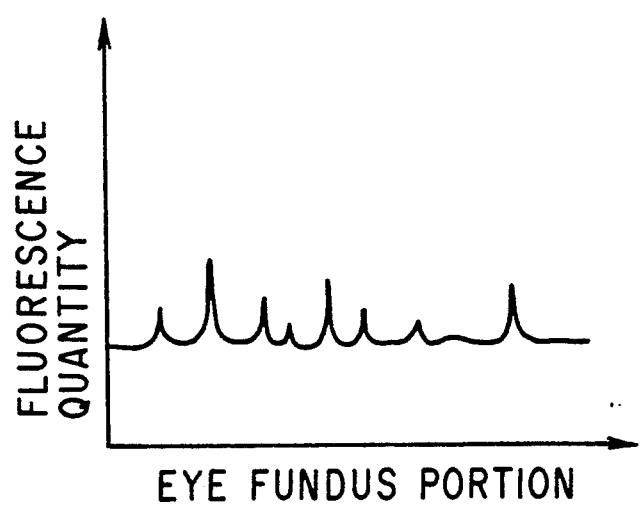
FIG. 5 is a graph showing the quantity of fluorescence of the eye fundus which appears in the middle time period.

By the way, in the initial time period T1, an intensive fluorescence begins to appear from a portion of the eye fundus Er, contrast is high and degree of increase of the fluorescence is large at a portion of the eye fundus Er as shown in FIG. 4. Also, in the middle time period T2, although an intensive fluorescence appears on the entire eye fundus Er, contrast is low and degree of increase of the intensity of the fluorescence is small as shown in FIG. 5. In the latter time period T3, the fluorescence becomes weak and contrast becomes gradually low.

Therefore, by splitting the area sensor I into a plurality of portions and watching the changes of the light receiving signal at such split portions, the initial time period T1, the middle time period T2 and the latter time period T3 can be judged. Also, by finding contrast of such split portions from a difference between the peak level and the lowest level of each of such split portions of the area sensor I, the initial time period T1, the middle time period T2 and the latter time period T3 may be judged from the contrast.

Also, the controller 70 is adapted to control the illumination light source 41, the photographing light source 42, the various cameras 14, 15, 13, K. etc. based on signals output from the joy stick switch 61, the light quantity comparing portion 71 and the set portions 72, 73, etc.

Operation of the ophthalmological taking instrument is described as follows.

When fluorescence photography is performed, a fluorescent agent is injected into the vein of the patient first. Then, when the eye fundus Er is photographed with, for example, infrared fluorescence, the infrared fluorescence mode switch 53 is activated. Then, the solenoid 77 is controlled by the controller 70 and the infrared fluorescence exciter filter 44 are inserted into the optical path. On the other hand, the mirror 11 is moved to the position shown by the broken line, and the barrier filter B4 is inserted into the optical path. And the illumination light source 41 is flashed and the eye fundus Er is illuminated with infrared light through the infrared fluorescence exciter filter 44.

After the passage of a predetermined time from when the vein injection is effected, fluorescence appears on a portion of the eye fundus Er by means of illumination of the infrared light as shown in FIG. 4. And the fluorescence reaches the CCD 14 through the objective lens 3, the perforated mirror 31, the focusing lens 4, the half mirror H, the relay lens 12, and the mirror 13, and an image of the eye fundus Er can be observed through the monitor 17.

On the other hand, the fluorescence reaches the area sensor I through the half mirror H and the barrier filter B4, and the area sensor I outputs a light receiving signal corresponding with the received light. And by this light receiving signal, the controller 70 causes the display 79 to display the fact that the area sensor I has detected the fluorescence. The examiner can tell that it has entered into the initial time period T1 from the display 79. Thus, the examiner can know the timing to photograph accurately.

By the way, at a stage of the initial time period T1 of the circulation time of the fluorescent agent on the eye fundus Er, brightness of the whole eye fundus Er is low but degree of increase of fluorescence emitted from a portion of the eye fundus Er is large. Accordingly, degree of increase of a light receiving signal output from the area sensor I corresponding to that portion also becomes large.

The controller 70 judges the initial time from the degree of increase of the light receiving signal, and the infrared fluorescence barrier filter B2 is not inserted into the photographing optical path unless the joy stick switch 61 is depressed. Therefore, although brightening degree of the eye fundus Er caused by the fluorescence is low, the image of the eye fundus Er observed through the monitor 17 is bright because the infrared fluorescence barrier filter B2 is not inserted into the optical path. Therefore, it is easy to perform alignment and focusing while observing the image of the eye fundus Er.

When the joy stick switch 61 is pressed in this initial time period T1, the solenoid 76 is actuated and the barrier filter B2 is inserted into position of the taking optical path shown by the broken line of FIG. 1. Also, the taking light source 42 is flashed and photography is performed by the still picture recording unit 15. When the photographing is over, the solenoid 76 is stopped and the barrier filter B2 is removed from the photographing optical path and moved to the position shown by the solid line. When the sensibility of the CCD 14 is good and a sufficient amount of exposure can be obtained from the light quantity of the illumination light source 41, it is unnecessary to flash the photographing light source 42.

When fluorescence from the eye fundus Er becomes strong or intensified and contrast of this fluorescence becomes small, the controller 70 judges it as the middle time period T2. Then, the solenoid 76 is actuated and the barrier filter B2 is inserted into the photographing optical path. And in case the still picture recording device switch 56 is in its pressed position, if the joy stick switch 61 is continuously pressed several times, photography is performed by the still picture recording device 15 every time the joy stick switch 61 is pressed. In this case, the barrier filter B2 is kept inserted in the photographing optical path and never removed from the photographing optical path each time photography is over. That is, the controller 70 functions as control means for keeping the barrier filter B2 in the photographing optical path.

Although the photographing light source 42 is not flashed in the middle time period T2 because a sufficient light quantity can be obtained, the light source 42 may be designed to be flashed.

If the joy stick switch 61 is pressed when the VTR switch 55 is in its pressed position, photography is performed by the VTR 16. In this case, the photographing light source 42 is not flashed either. And when the joy stick switch 61 is pressed again, photography by the VTR 16 is stopped.

When the fluorescence from the eye fundus Er becomes weak, the controller 70 judges it as the latter time period. Then, the solenoid 76 is stopped and the barrier filter B2 is removed from the photographing optical path. The joy stick switch 61 is pressed every few minutes, and every time the joy stick switch 61 is pressed, photography is performed by the still picture recording device 15. In this case, every time the joy stick switch 61 is pressed, the solenoid 76 is actuated and the barrier filter B2 is inserted into the photographing optical path, and the filter B2 is removed from the photographing optical path each time photography is over. Also, photographing light source 42 is flashed every time the joy stick switch 61 is pressed.

By the way, when it is in the latter time period, fluorescence from the eye fundus Er becomes weak. However, as the barrier filter B2 is removed from the taking optical path while photography is not being performed, the image of the eye fundus Er observed through the monitor 17 is bright. Therefore, alignment and focusing can be easily performed.

In this way, as the insertion and removal of the barrier filter B2 into and from the photographing optical path are automatically performed in such a manner as to match with the initial time period, middle time period or latter time period of the circulation time of the fluorescent agent, no operation for insertion and removal of the barrier filter B2 is required.

When the barrier filter light quantity interlocking switch 48 is being pressed, the barrier filter B2 is kept inserted in the photographing optical path during the initial and middle time periods. And every time the joy stick switch 61 is pressed, the photographing light source 42 is flashed and the eye fundus is taken in the same manner as mentioned above. In this case, like the above, as the insertion and removal of the barrier filter B2 into and from the taking optical path are automatically performed, no operation for insertion and removal of the barrier filter B2 is required.

Next, there will be described operation for controlling the barrier filter B2 based on the time counted by the timer 75.

First of all, a start time for the middle time period T2 and an end time for the middle time period T2 are set by the set switch 46. After the vein injection is effected, the barrier filter time interlocking switch 47 is pressed and, for example, the infrared fluorescence mode switch 53 is actuated. As a result, the solenoid 77 is controlled by the controller 70, the infrared fluorescence exciter filter 44 is inserted into the optical path and the illumination light source 41 is flashed. And the eye fundus Er is illuminated with infrared light by the infrared fluorescence exciter filter 44.

And every time the joy stick switch 61 is pressed, the solenoid 76 is controlled and the barrier filter B2 is inserted into the photographing optical path. The taking light source 42 is flashed and the eye fundus Er is taken in the same manner as mentioned above.

On the other hand, the timer 75 starts counting from the time point when the barrier filter time interlocking switch 47 is pressed. When the time counted by the timer 75 becomes the time (middle time interval T2) set by the time set switch 46, the solenoid 76 is actuated by the controller 70 and the barrier filter B2 is inserted into the photographing optical path during the middle time period T2. Every time the joy stick switch 61 is pressed, the eye fundus Er is photographed. In this case, the barrier filter B2 is not removed from the photographing optical path every time one photography is over.

When the time counted by the timer 75 indicates the end of the middle time period, the solenoid 76 is stopped and the barrier filter B2 is removed from the photographing optical path. Thereafter, the barrier filter B2 is controlled in the same manner as described above and the eye fundus Er is taken.

In this way, as the insertion and removal of the barrier filter B2 into and from the photographing optical path are automatically performed in accordance with the initial, middle and latter time periods of circulation time of the fluorescent agent based on the time counted by the timer 75, no operation for insertion and removal is required.

In the above embodiment, the infrared fluorescence mode switch 52 is selected. However, when the visible fluorescence mode switch 52 is selected, the visible fluorescence mode switch 43 is inserted into the illuminating optical path and the visible fluorescence barrier filter B1 is controlled to be inserted and removed into and from the photographing optical path in accordance with the circulation time of the fluorescent agent in the same manner as mentioned above.

In this case, as the mirror 11 is not inserted in the position shown by the broken line in the initial time period T1 or in the latter time period T3 unless at least photography is undergoing, fluorescence emitted from the eye fundus Er reaches the eyepiece S through the objective lens 3, the perforated mirror 31, the focusing lens 4, the half mirror H, the relay lens 5, the taking lens 6, and the mirror 8,9, and the eye fundus Er can be observed through the eyepiece S.

Although the fluorescence from the eye fundus Er becomes weak in the initial time period T1 and in the latter time period T3, the barrier filter B2 is removed from the taking optical path in the same manner as mentioned above. Therefore, the eye fundus Er can be observed in its bright state and alignment and focusing can be easily performed.

When photography is performed with the instant camera 23 and the 35 mm camera K in the visible fluorescence photographing mode, the photographing light source 42 is flashed every time photograph is performed in the respective time periods T1, T2, and T3.

In the above embodiment, when the joy stick switch is depressed, the barrier filters B1 and B2 are inserted into the photographing optical path. Alternatively, it may be designed such that the barrier filters B1 and B2 are inserted into the photographing optical path when the area sensor detects fluorescence.

What is claimed is:

1. An ophthalmological photographing instrument including photographing means for imaging the fundus of an eye to be tested when a photographing switch is actuated, and a barrier filter means for insertion into a photographing optical path when a fluorescent agent has been introduced into a patient's eye fundus and a fluorescence photography is performed, said ophthalmological photographing instrument comprising:
    a light receiving sensor for receiving fluorescent light emitted from the eye fundus and for generating a signal in accordance with the fluorescent light received; and
    control means for inserting said barrier filter into said photographing optical path when said photographing switch is actuated and when said light receiving signal generated by said light receiving sensor becomes smaller than a predetermined value.

2. An ophthalmological photographing instrument including photographing means for imaging the fundus of an eye to be tested every time a photographing switch is actuated, and a barrier filter for insertion into a photographing optical path when a fluorescent agent has been introduced into a patient's eye fundus and a fluorescence photography is performed, said ophthalmological photographing instrument comprising:
    judgment means for determining an initial time period where fluorescence appears on the eye fundus, a middle time period where the fluorescence begins to spread over the entire eye fundus, and a latter time period where the fluorescence becomes gradually weaker; and
    control means for controlling insertion and removal of said barrier filter into and from said photographing optical path in accordance with the time period determined by the judgment means.

3. An ophthalmological photographing instrument according to claim 2, including a light receiving sensor for receiving fluorescent light emitted from the eye fundus and for generating a signal in accordance with the fluorescent light received, wherein said judgment means comprises a controller for determining the initial time period, middle time period and latter time period based on said signal generated by said light receiving sensor.

4. An ophthalmological photographing instrument according to claim 2, wherein said judgment means includes a timer for counting and setting intervals between said time periods and a controller for determining the initial time period, middle time period and latter time period from the intervals counted by said timer.

5. An ophthalmological photographing instrument according to claim 2, wherein said control means functions to retain said barrier filter in said photographing optical path during the time period which is determined by said judgment means as the middle time period.

6. An ophthalmological photographing instrument according to claim 1, wherein said light receiving sensor comprises an area sensor.

7. An ophthalmological photographing instrument according to claim 3, wherein said light receiving sensor comprises an area sensor.

8. An ophthalmological photographing instrument according to claim 2, wherein said control means is actuated to control insertion and removal of said barrier filter only during said latter time period as determined by said judgment means.

9. An ophthalmological photographing instrument including still picture photographing means for imaging the fundus of an eye to be tested as a still picture, moving picture photographing means for imaging the eye fundus as a moving picture, selection means for selecting either said still picture photographing means or said moving picture photographing means, and a barrier filter for insertion into a photographing optical path of said still picture and said moving picture photographing means when a fluorescent agent has been introduced into a patient's eye fundus and a fluorescence photography is performed, said ophthalmological photographing instrument further including:
    means for determining when the fluorescent agent on the patient's eye fundus provides optimal contrast for purposes of imaging the fundus; and
    control means, responsive to said determining means, for retaining said barrier filter in said photographing optical path while imaging of the fundus is being performed by said moving picture photographing means.

10. An ophthalmological photographing instrument including photographing means for imaging the fundus of an eye to be tested when a photographing switch is actuated, and a barrier filter means for insertion into a photographing optical path when a fluorescent agent has been introduced into a patient's eye fundus and a fluorescence photography is performed, said ophthalmological photographing instrument comprising:
- detection means for detecting fluorescence emitted from the eye fundus when the fluorescent agent is present thereon; and
- insertion means for automatically inserting said barrier filter into said photographing optical path when said detection means detects fluorescence.

* * * * *